(12) United States Patent
Marissen

(10) Patent No.: US 7,291,172 B2
(45) Date of Patent: Nov. 6, 2007

(54) ARTIFICIAL INTERVERTEBRAL DISC

(75) Inventor: Roelof Marissen, Born (NL)

(73) Assignee: DSM IP Assets B.V., TE Heerlen (NL)

( * ) Notice: Subject to any disclaimer, the term of this patent is extended or adjusted under 35 U.S.C. 154(b) by 0 days.

(21) Appl. No.: 10/534,100

(22) PCT Filed: Nov. 28, 2003

(86) PCT No.: PCT/NL03/00842

§ 371 (c)(1),
(2), (4) Date: Jul. 6, 2005

(87) PCT Pub. No.: WO2004/049980

PCT Pub. Date: Jun. 17, 2004

(65) Prior Publication Data

US 2005/0256580 A1 Nov. 17, 2005

(30) Foreign Application Priority Data

Nov. 29, 2002 (NL) .................................... 1022023

(51) Int. Cl.
*A61F 2/44* (2006.01)
(52) U.S. Cl. ............................... 623/17.12; 623/11.11; 623/17.16

(58) Field of Classification Search ............. 623/11.11, 623/17.11–17.16, 23.64–23.67
See application file for complete search history.

(56) References Cited

U.S. PATENT DOCUMENTS

| 5,957,974 | A | * | 9/1999 | Thompson et al. ......... 623/1.13 |
| 6,066,154 | A | * | 5/2000 | Reiley et al. ............... 606/192 |
| 6,416,776 | B1 | | 7/2002 | Shamie |
| 6,733,531 | B1 | * | 5/2004 | Trieu ....................... 623/17.11 |
| 2002/0026244 | A1 | | 2/2002 | Trieu |
| 2004/0138762 | A1 | * | 7/2004 | Therin et al. ............. 623/23.75 |

FOREIGN PATENT DOCUMENTS

| EP | 0 346 129 | 12/1989 |
| WO | WO 02/34169 | 5/2002 |

* cited by examiner

*Primary Examiner*—David J Isabella
(74) *Attorney, Agent, or Firm*—Nixon & Vanderhye PC

(57) ABSTRACT

Artificial intervertebral disc, comprising a nucleus of flexible material with the shape of a flattened body, with a lower and an upper side connected by a lateral surface, having a rounded-preferably circular or ellipsoid-shape, around which at least substantially radially oriented windings of a traction-resistant fibre have been applied. The fibres have a tensile strength of at least 1 GPa and a modulus of at least 10 GPa.

20 Claims, 2 Drawing Sheets

ARTIFICIAL INTERVERTEBRAL DISC

Figure 1:
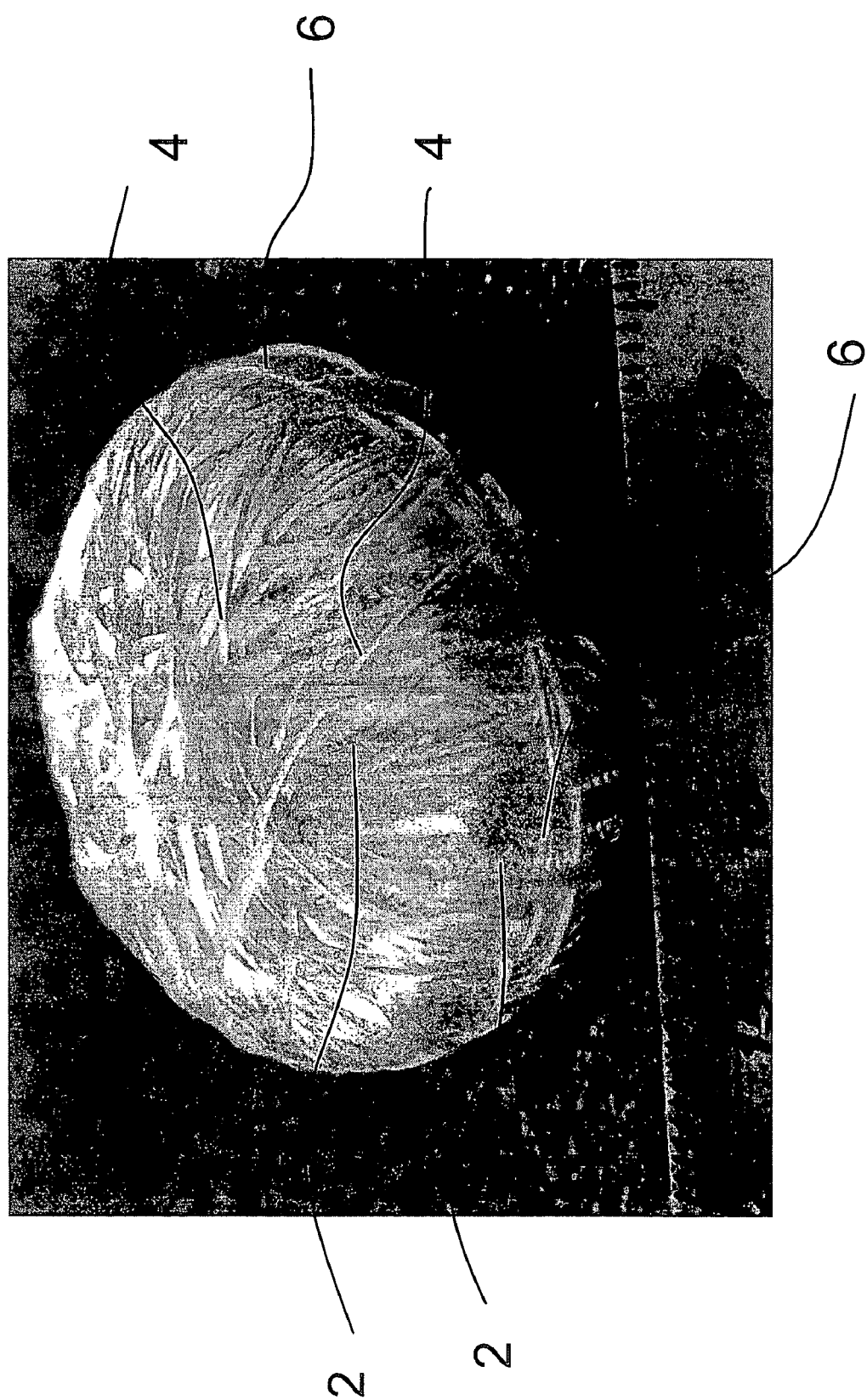

This application is the U.S. national phase of international application PCT/NL2003/000842 filed 28 Nov. 2003 which designated the U.S. and claims benefit of NL 1022023, dated 29 Nov. 2002, the entire content of which is hereby incorporated by reference.

The invention relates to an artificial intervertebral disc.

Such a disc is known from U.S. Pat. No. 6,375,682. The known disc consists of two metal plates positioned opposite each other, each of which lies against the facing sides of the bodies of two successive vertebrae and each being connected thereto, and an intermediate system of bellows and springs which permits movement between the metal plates and the vertebral bodies connected with these.

The known construction presents the drawback that it is mechanically complex and that as a result of the use of hard materials, such as metals in contact with body parts, it can give rise to adaptation problems.

The aim of the invention now is to provide an artificial intervertebral disc, which to a high extent prevents the drawbacks of the known disc.

This aim is achieved according to the invention in that the disc contains a nucleus of a flexible material around which windings of a traction-resistant fibre have been applied.

The disc according to the invention is of a simple construction, only contains relatively soft materials and, due to the flexibility of the nucleus, conforms well to the vertebral bodies between which the disc is placed. A further advantage is that the disc according to the invention can extend over a large part or even the entire surface of the vertebral bodies, so that the forces occurring in the vertebral column are born by virtually the entire vertebral body. In connection with the required mutual mobility the known discs as a rule are considerably smaller than the vertebral bodies between which they are placed, so that high local loads may occur therein. The disc according to the invention can be as large as the vertebral bodies and then still permit a high degree of mutual mobility of the vertebral bodies.

The disc according to the invention comprises a flexible nucleus with the shape of a flattened body, with a lower and an upper side, connected by a lateral surface. By 'flexible' is understood here that the material has a low shear modulus. This modulus preferably is at most 50 MPa, more preferably at most 20 MPa. The modulus can in fact be lowered with hardly any restriction, but a shear modulus of less than 1 MPa entails the necessity of extra measures in order to enclose the nucleus virtually liquid tight. The elongation at break of the nucleus preferably is higher than 20%, more preferably higher than 100%. An upper limit to this property is in fact determined by the availability of materials, but under normal conditions of use the nucleus will not be loaded beyond the above-mentioned rates of elongation. Further, the nucleus has a low compressibility. The compressibility can be seen as the inverse of the bulk modulus. A bulk modulus of 1 GPa will in general be amply sufficiently high already. This is offered by virtually all rubber and gel-like materials, provided they contain little air or other gases. With such a nucleus, local load variations, for instance when the vertebral column is bent, are converted into shape variations of the entire nucleus. Thus, pressing down of material by a local load at one spot will result in protrusion at another spot where the load is absent. This behaviour corresponds to a high degree to the functioning of the natural nucleus in intervertebral discs.

The nucleus has the shape of a flattened body with a lower and an upper side. By 'flattened' is understood here that the perpendicular distance between lower and upper side is considerably smaller, for instance by at least a factor 2, than the dimensions in the directions perpendicular to said distance. As a matter of fact, the lower and the upper side need not be completely flat, but may for instance have a central section, which is thicker or thinner than a marginal area, giving the nucleus the shape of a lens for instance. The lower and the upper side of the nucleus preferably have a rounded shape; by this is meant that the edge of these sides in the plane thereof has no pointed or angular parts, for instance due to the smallest radius of curvature in the edge being at least 10 mm. With this it is achieved that the pressures occurring when the disc is under load are distributed evenly over the windings, which considerably reduces the risk of local protuberances. More preferably, the lower and the upper side are of a circular or ellipsoid shape, with which the most even pressure distributions along the side surface—in the following also referred to as the 'lateral surface'—are achieved. Further, the nucleus can have a hole in its centre, giving it the shape of a torus or a corresponding shape.

Suitable materials for the nucleus preferably are biocompatible materials, for instance silicone rubber, of the type which is already widely used for implants, polyurethane rubber, acrylate rubber, EP(D)M rubber and other rubber-like or gel-like materials. Biocompatibility of the rubber is not a strict condition, however, provided that the rubber is packed in an impervious biocompatible film. But the materials should at all times meet the above-mentioned conditions in terms of flexibility in combination with a low hydrostatic compressibility. The nucleus can therefore even be in the form of a liquid enclosed in a biocompatible capsule, which should in itself be sufficiently flexible to undergo the shape variations induced by loading.

Around the nucleus windings of a traction-resistant fibre have been applied in an at least substantially radial direction. The windings thus applied around the nucleus do permit some shape variations of the nucleus in the longitudinal direction of the vertebral column, but not or only hardly in the direction perpendicular thereto. In this way it is avoided that the load-induced shape variations of the nucleus result in protuberances of the nucleus out of the vertebral body. The scope of shape variation (flexibility) in the longitudinal direction of the vertebral column appears to be greater at low loads than at high loads. The nucleus in the disc according to the invention thus appears to have a progressive longitudinal resilience profile. This is a major advantage as the high initial flexibility in the longitudinal direction ensures good shock absorption, while the declining flexibility under higher loads ensures that the distance between the vertebrae remains sufficient to prevent strangulation of nerves.

The windings substantially run in a radial direction. By this is understood that the windings run across the lower and the upper side, with at least 50% of the windings across the lower and the upper side following a path whose smallest distance to the centre of gravity of the lower and the upper side is at most equal to 30% of the largest dimension of the lower and the upper side. Further, the windings on their way from the lower to the upper side run across the lateral surface. The fibres preferably run across the lateral surface at an angle, which deviates at most 55° from the direction perpendicular to the shortest connection between lower and upper side. It is of advantage when the fibres across the lateral surface have different angles to the perpendicular direction. Fibres with small angles have a strong stabilizing effect on the nucleus. Fibres with an angle of 45° are optimal as regards bearing of torsion loads that can occur between two vertebrae. The fibres thus substantially run along geodetic lines, which are the shortest connecting lines between two points on the surface of the nucleus. The above-described fibre direction variations on the upper and the lower side offer the advantage that an accumulation of fibres and thus a local thickening at the centre of gravity is prevented. Said variations on the lateral surface offer the advantage that torsion forces exerted on the disc are born effectively. It is thus also avoided that the tensile forces exerted on the fibres due to loading of the nucleus easily result in a shift of the fibres to a shorter path across the nucleus. Such a shift could lead to an undesirable diminution of the resistance to the occurrence of protuberances.

For additional suppression of possible shifting of the windings upon loading it is of advantage if the successive windings are not completely placed on top of each other, but instead the fibre of a winding alternately runs a few times under and over previously placed windings. Impregnation with a glue-like substance can also help to prevent said shifts. For such impregnation it is of advantage to use a biocompatible tissue glue because it promotes the adhesion of the disc to the vertebral bodies.

Besides the substantially radially running windings, preferably windings of a traction-resistant fibre are also present which run completely across the lateral surface. This provides an additional barrier against the occurrence of protuberances of the nucleus out of the disc.

Further improvement of the resistance of the disc against the occurrence of protuberances can be achieved due the presence of a fabric between the nucleus and the windings of the traction-resistant fibres along at least the lateral surface and at least a part of the lower side and a part of the upper side. The fabric preferably is so densely woven that, in combination with the presence of the fibres wound around it, no nucleus material can escape from the fabric upon loading. If with a given combination nucleus material would escape as a result of a load that may occur in practice, this can be simply remedied by a person skilled in the art by choosing a denser fabric and/or a denser winding pattern. It is also possible to choose a material with a higher shear modulus within the limits defined elsewhere herein.

From U.S. Pat. No. 5,824,093 a prosthesis is known for replacement of the nucleus in a natural intervertebral disc, which prosthesis consists of a hydrogel core surrounded by a woven pouch. After removal of the natural nucleus from the intervertebral disc, two prostheses are placed in the space that has thus become available. The prostheses do not fill the entire space, which already restricts the risk of protuberance. Further, the natural annulus is still present which previously encapsulated the natural nucleus and now the prostheses. Said document does not provide any indication for the construction of a prosthesis for the entire intervertebral disc, leave alone the construction of the intervertebral disc according to the invention. Moreover, encapsulation of the nucleus in the disc in accordance with the invention in solely a woven pouch is absolutely insufficient for the prevention of protuberance of the nucleus upon loading. This is mainly due to the availability of much room for shifting of the fibres and to the high construction stretch in a fabric. Moreover, the fibre length in such a fabric is small, of the order of magnitude of the pouch. Load build-up in the fibres usually requires a larger length. The strength of the fibres in such a pouch consequently is utilized insufficiently. In the disc according to the invention the windings running across the lower and the upper side preferably form part of a single long filament. If several filaments are used, the length thereof is preferably equal to at least 10 times the circumference of the nucleus, measured along a geodetic line running over the centre of gravity. The optional windings across the lateral surface also preferably consist of a single filament. If several filaments are used for this, the length of each one is preferably equal to at least 10 times the circumference of the nucleus, measured across its lateral surface.

A fibre is deemed to be traction resistant within the present context if the elongation at break is at most 15%, preferably at most 5%. The fibre also preferably has a shear modulus of at least 10 GPa, preferably at least 75 GPa, and a tensile strength of at least 1 GPa, preferably at least 2 and even 2.5 GPa.

The material of the fibres should be tolerated by the body, not cause any infection, decomposition or other negative reactions in it and not be dissolved, decomposed or otherwise degraded in it. Suitable materials therefore are for instance polyethylene, in particular of the high-molar mass type, aramid, carbon, polybenzoxazoles, poly(2,6-diimidazo [4,5-b4',5+-e]pyridinylene-1,4(2,5-dihydroxy)phenylene) and polyethylene terephthalate. Fibres of other materials meeting said requirements are also suitable for application in the disc according to the invention.

The thickness of the fibre of which the windings consist can vary within wide limits, for instance between 50 dtex and 2000 dtex, and it can be a monofilament as well as a multifilament fibre. In general a better encapsulation of the nucleus is obtained if a given amount of fibre material is present in the windings in the form of more windings of a thinner fibre than in the form of proportionately fewer windings of a thicker fibre. In the former case the structure is denser than in the latter, given an even winding pattern.

Further, on or onto the fibre material substances or compounds can be applied which promote the growing in of bone tissue, from a vertebral body with which the disc is in contact, on or between the windings or on or between any fabric that is present. This will promote the fixation of the disc relative to the adjacent vertebral bodies. For the purpose of initial fixation of the disc of the invention relative to the vertebral bodies between which it has been placed the disc can be provided with protrusions oriented towards the vertebral bodies.

The artificial intervertebral disc according to the invention can be manufactured by applying the fibres around the nucleus in the desired pattern as described in the foregoing. This can be done by hand as well as with the help of machines equipped for this purpose. The nucleus can be impregnated or otherwise treated to comprise compounds like growth improvers, inflammation inhibitors, antibiotics and other compounds having a desired action on the human body.

It will be clear to the skilled person that, although the foregoing described an artificial intervertebral disc only, a disc or body of similar construction but of different shape may also be suitable for use in other applications; including but not limited to other medical applications, like prostheses. The shape and dimensions of such disc or other body can be adapted to its specific use; like for example an artificial knee meniscus.

Figure 2:
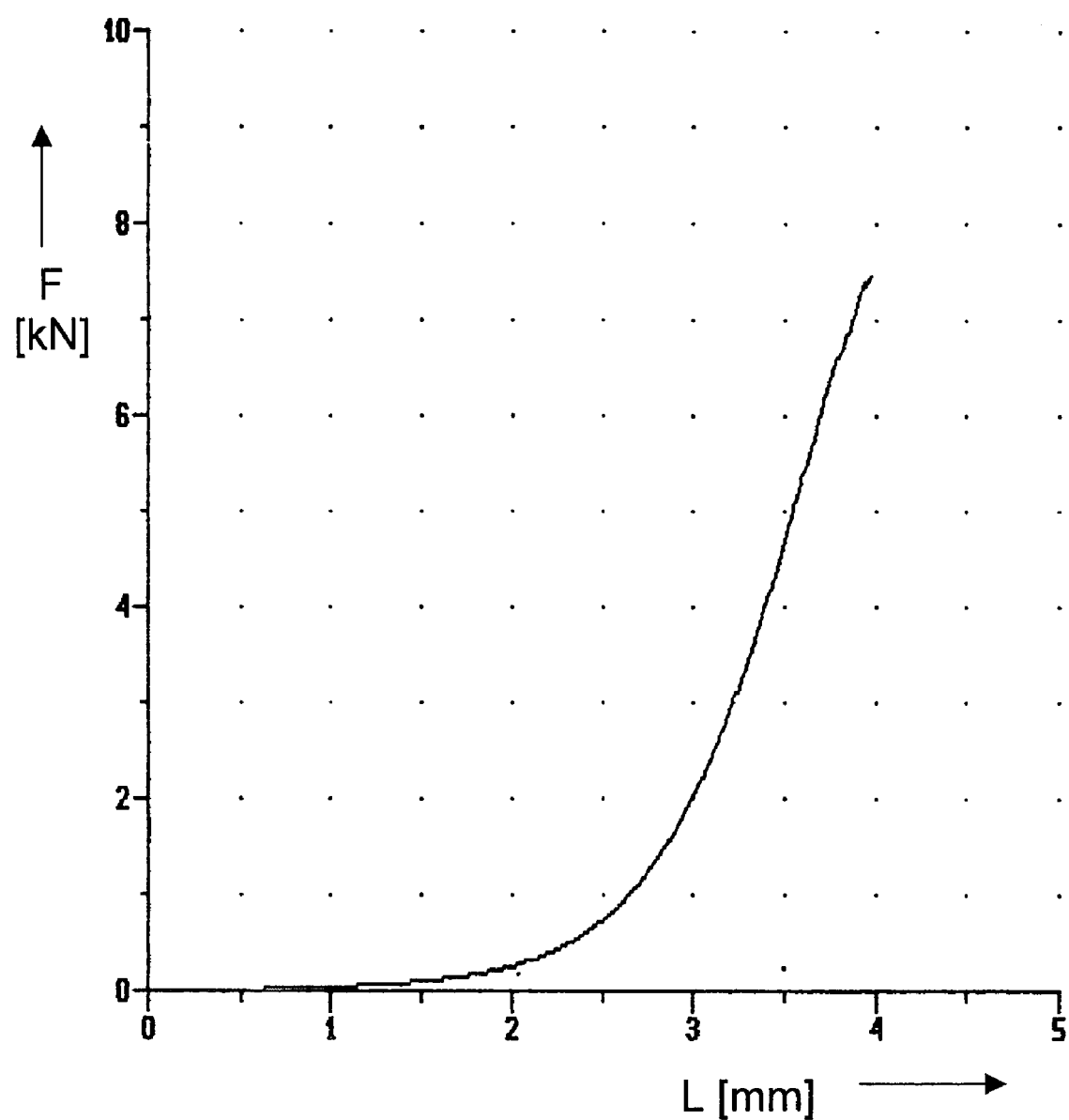

The invention will now be elucidated with reference to the following figures, wherein FIG. 1 is a photo of a manually wound disc according to the invention, and FIG. 2 is a force vs. displacement curve measured on the disc of FIG. 1.

In FIG. 1 the non-visible nucleus in the form of a cylindrical disc with a diameter of 38.5 mm and a thickness of 15 mm and made of a silicone rubber with a shear modulus of about 5 MPa, an elongation at break of about 200% and a bulk modulus of about 1.5 GPa has been encapsulated with a fabric 2 of traction-resistant polyethylene fibres, which fabric is just visible yet at some spots between the windings 4 and 6. Around this there are both windings 4, which run across the lower and the upper side and the lateral surface, and windings 6 which only run across the lateral surface. The fibres consist of two twisted multifilaments of 440 dtex each and made of high-molecular polyethylene. The fibres that have been used for the fabric and the windings consist of a gel-spun high-molecular PE with a tensile strength of 3.6 GPa and a modulus of 115 GPa. The elongation at break is 3.5%.

In FIG. 2 the force F in kN with which the disc of FIG. 1 was loaded in a Zwick 1484 universal testing machine has been plotted against the yielding L in mm caused by this load. It can clearly be seen that after the run-up section up to 1 mm of displacement, in which the disc is clamped in, in the first section from 1 to approx. 2-2.5 mm of the load curve only a small force is needed for a certain displacement, while in the last section, from 2.5 mm, the required force increases very much. This profile means that the disc has a high degree of flexibility in relation to small forces, in combination with a high capability to absorb with relatively very little yield strong forces exerted on the disc. It appears that the disc does not collapse until the force exerted on it exceeds 7 kN, corresponding to a load of about 700 kg, which is much higher than the forces to which the human vertebral column is exposed in practice.

The invention claimed is:

1. Artificial intervertebral disc comprising:
   a nucleus of flexible material with the shape of a flattened body having a lower surface, an upper surface, and a lateral surface connecting the lower and upper surfaces to one another, and
   at least one traction-resistant fibre having a length which is at least ten times a circumference of the nucleus, the fibre being continuously wound around each of the lower, upper and lateral surfaces forming substantially radially oriented continuous windings which run substantially along geodetic lines about the lower and upper surfaces of the flattened body.

2. Intervertebral disc according to claim 1, wherein the lower and the upper surfaces are of a rounded shape.

3. Intervertebral disc according to claim 1, wherein at least one traction-resistant fibre has a tensile strength of at least 1 GPa and a modulus of at least 10 GPa.

4. Intervertebral disc according to claim 1, wherein at least one traction-resistant fibre consists of polyethylene.

5. Intervertebral disc according to claim 1, comprising at least one laterally wound traction-resistant fibre which is wound completely around only the lateral surface of the flattened body.

6. Intervertebral disc according to claim 1, further comprising a fabric positioned between the nucleus and at least one traction-resistant fibre running along at least the lateral surface and at least parts of the lower and upper surfaces.

7. Intervertebral disc according to claim 6, wherein the fabric consists of traction-resistant fibres.

8. Intervertebral disc according to claim 7, wherein the traction-resistant fibres of the fabric have a tensile strength of at least 1 GPa and a modulus of at least 10 GPa.

9. Intervertebral disc according to claim 1, wherein the lower and the upper surfaces are of a circular shape.

10. Intervertebral disc according to claim 1, wherein the lower and the upper surfaces are of an ellipsoid shape.

11. Intervertebral disc according to claim 5, wherein at least one laterally wound traction-resistant fibre has a length which is at least ten times a circumference of the nucleus.

12. Intervertebral disc according to claim 1, comprising several traction-resistant fibres, each being of a length sufficient to be wound around the lower, upper and lateral surfaces, the fibre establishing substantially radially oriented windings on the lower and upper surfaces of the flattened body.

13. Intervertebral disc according to claim 5, comprising several laterally wound traction-resistant fibres, each being of a length sufficient to be wound completely around only the lateral surface of the flattened body.

14. An artificial intervertebral disc comprising:
   a nucleus of flexible material with the shape of a flattened body having a lower surface, an upper surface, and a lateral surface defining a circumference of the flattened body and joining the lower and upper surfaces to one another; and
   at least one traction-resistant fibre having a length which is at least ten times the circumference of the flattened body, the fibre being wound around the lower, upper and lateral surfaces of the flattened body and establishing substantially radially oriented windings which run substantially along geodetic lines on the lower and upper surfaces thereof.

15. The intervertebral disc as in claim 14, further comprising at least one lateral traction-resistant fibre having a length which is at least ten times the circumference of the flattened body and being wound around only the lateral surface thereof.

16. The intervertebral disc as in claim 15, wherein each traction-resistant fibre has a tensile strength of at least 1 GPa and a modulus of at least 10 GPa.

17. Artificial intervertebral disc comprising:
   a nucleus of flexible material with the shape of a flattened body having a lower surface, an upper surface, and a lateral surface connecting the lower and upper surfaces to one another,
   at least one traction-resistant fibre continuously wound around each of the lower, upper and lateral surfaces forming substantially radially oriented continuous windings which run substantially along geodetic lines about the lower and upper surfaces of the flattened body; and
   at least one laterally wound traction-resistant fibre having a length which is at least ten times a circumference of the nucleus which is wound completely around only the lateral surface of the flattened body.

18. Artificial intervertebral disc comprising:
   a nucleus of flexible material with the shape of a flattened body having a lower surface, an upper surface, and a lateral surface connecting the lower and upper surfaces to one another,
   at least one traction-resistant fibre continuously wound around each of the lower, upper and lateral surfaces forming substantially radially oriented continuous windings which run substantially along geodetic lines about the lower and upper surfaces of the flattened body; and
   several laterally wound traction-resistant fibres, each being of a length sufficient to be wound completely around only the lateral surface of the flattened body.

19. Artificial intervertebral disc comprising:
   a nucleus of flexible material having a modulus of at most 50 MPa and the shape of a flattened body with a lower surface, an upper surface and a lateral surface connecting the lower and upper surfaces to one another, and at least one traction-resistant fibre having a length which is at least ten times a circumference of the nucleus, the fibre being continuously wound around each of the lower, upper and lateral surfaces forming substantially radially oriented continuous windings which run substantially along geodetic lines about the lower and upper surfaces of the flattened body.

20. Intervertable disc according to claim 1 or 19, wherein the continuous windings across the lower and upper surfaces of the flattened body are substantially radially oriented such that at least 50% of the windings follow a path whose smallest distance to a center of gravity of the lower and upper surfaces is at most equal to 30% of a largest dimension of the lower and upper surfaces.

* * * * *